(12) United States Patent
Munck et al.

(10) Patent No.: US 6,316,562 B1
(45) Date of Patent: Nov. 13, 2001

(54) CATALYST SYSTEMS FOR (CO-) POLYMERIZATION REACTIONS, METALLOCENE AMIDE HALOGENIDES, THE PRODUCTION AND USE THEREOF

(75) Inventors: Florian Munck, Germering; Werner Zeiss, Eurasburg; Christoph Hartmann, Oberhaching; Alexander Vogel; Andreas Detig, both of München, all of (DE)

(73) Assignee: Peroxid-Chemie GmbH & Co. KG, Pullach (DE)

( * ) Notice: Subject to any disclaimer, the term of this patent is extended or adjusted under 35 U.S.C. 154(b) by 0 days.

(21) Appl. No.: 09/445,198

(22) PCT Filed: Jun. 8, 1998

(86) PCT No.: PCT/EP98/03406

§ 371 Date: Jan. 21, 2000

§ 102(e) Date: Jan. 21, 2000

(87) PCT Pub. No.: WO98/56831

PCT Pub. Date: Dec. 17, 1998

(30) Foreign Application Priority Data

Jun. 10, 1997 (DE) .............................. 197 24 465

(51) Int. Cl.⁷ ...................................... C08F 4/44
(52) U.S. Cl. .................... 526/160; 526/159; 526/170; 502/152; 502/158; 502/167; 502/169; 502/200; 556/56; 556/63
(58) Field of Search ................... 526/159, 160, 526/170; 502/152, 158, 167, 169, 200; 556/56, 63

(56) References Cited

U.S. PATENT DOCUMENTS 4,728,706 3/1988 Farnham et al. .

FOREIGN PATENT DOCUMENTS 0519746 12/1992 (EP) .
0745617 12/1996 (EP) .

OTHER PUBLICATIONS

Gambarotta et al., J. Am. Chem. Soc. vol. 107 (22), p. 6280, 1985.*
Walsh et al., J. Am. Chem. Soc. vol. 113 (16), p. 6344, 1991.*
Froeberg et al. J. Organomet. Chem., vol. 280 (3), p. 358, 1985.*
Baye, Synth. React. Inorg. Metal–Org. Chem., vol. 5 (2), p. 96, 1975.*
Coles et al., Synlett, Feb., 1992, p. 144.*
Nichia Kagaku Kogyo KK, Prepn. of halogenated metallocene cpd . . . either and amine, JP–05239081–A.
Brenner, et al. Mixed Chloro(dialkylamino) Complexes . . . Z. anorg. allg. Chem. 621 (1995), 2021–2024.
Chem. Absts. vol. 122, 1995 No. 291763q.
Search Report on 10 Chemical Abrsts. citations with structures (pp. 1–15).
Sinnema et al.—"Linked Cyclopentadienyl . . . " Journ. of Molecular Catalysis—vol. 128, 1998, pp. 143–153.
Buerger, et al.—"Titanium–nirogen . . . "—J. Organomet. Chem (1975), 101(3) 295–306.
Coles et al. "Alpha–Alkylation . . . " (1992) (2) 143–5.
Walsh, et al.—"Generation dative . . . " J. Am Chem.Soc, (1991), 113 (16), 6343–5—p. 6344.
Gambarotta, et al.—"Stepwise reduction . . . " J. Am. Chem. Soc. 1985 107 (22), 6278–82—p. 6280.
Froemberg—"Reactions of . . . " J. Organomet. Chem. (1985), 280(3) 355–63, p. 358,par. 4–p. 359.
Baye—"Reactions of . . . " Synth. React. Inorg. Met–Org Chem 1975, 5 (2), 95–102.
Thiyagarajan, et al.—"Synthesis, Structure Dynamic Properties, and Indenyl Transfer . . . " Organometallics (1998).

* cited by examiner

Primary Examiner—David W. Wu
Assistant Examiner—William K Cheung
(74) Attorney, Agent, or Firm—Fulbright & Jaworski, LLP

(57) ABSTRACT

This invention relates to new metallocenes with mixed substituents and enhanced activity, methods of producing metallocene compounds, and the use of metallocenamide halides for generating an active catalyst system for (co) polymerization reactions.

28 Claims, No Drawings

CATALYST SYSTEMS FOR (CO-) POLYMERIZATION REACTIONS, METALLOCENE AMIDE HALOGENIDES, THE PRODUCTION AND USE THEREOF

This invention relates to catalyst systems for (co) polymerization reactions, containing new metallocenes with mixed substituents, the metallocenes themselves, a new method of producing metallocene compounds, and the use of metallocenamide halides for generating a catalyst system in keeping with the invention.

Polyolefin plastics have been part and parcel of our modern society ever since the discoveries of Ziegler and Natta were implemented industrially. By skillful choice of different monomers, materials can be produced which contrast with each other primarily in their different properties. The use of single-site catalysts allowed great progress to be made in obtaining further improved polymers and understanding polymerization reactions at molecular level. Combined with a co-catalyst, these polymerization initiators, also known generally as metallocenes, are highly active starters in the linking of monomers to form chains, and because of their uniform chemical and structural characteristics, guarantee a given, defined polymer or copolymer structure.

The synthetic pathway to these catalysts thus plays, so to speak, a key role, and now that chemical research has been carried out in this field with increasing intensity for some 15 years now, there are now many publications and patents describing such syntheses.

The use of metallocene dichlorides A to generate active catalyst systems, eg, with methylaluminoxan (MAO), is prior art. Strictly speaking, the metallocene dichloride is only a catalyst precursor.

  (A)

  (B)

The corresponding metallocene diamides B (X=NMe$_2$), by contrast, have so far not been used successfully in (co)polymerization reactions. In both the formulas A and B, L stands for metallocene ligand.

Even if the use of metallocene dichloride A already provided a means of generating an active catalyst system, there was still a need for improved catalysts which show higher activity or have other advantages compared to the catalysts known so far.

This object is established according to the invention by provision of a catalyst system for (co)polymerization reactions, which contains a metallocenamide halide with the formula (I)

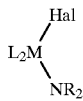

in which
L is a metallocene ligand,
Hal is a halogen from the group comprising F, Cl, Br and I,
M is a metal from group III, IV or V of the periodic table or from the lanthanide series, and
R stands for identical or different, straight-chain or branched, saturated or unsaturated hydrocarbon radicals with up to 8 carbon atoms, where the amido group NR$_2$ can also form a heterocycle with up to 8 carbon atoms, maybe incorporating further heteroatoms, and a co-catalyst.

Within the framework of this invention, it was surprisingly found that the (co)polymerization results could be improved drastically by using metallocenamide halides of formula I in a catalyst system. After activation by MAO, eg, these show much higher activity than do metallocene dichlorides, even when only small quantities of MAO are used.

In especially preferred embodiments of the invention, the metallocenamide chlorides which have the formula 1 and are contained in the catalyst system of the invention have titanium, zirconium or hafnium as metals.

In particularly preferred metallocenamide halides of formula 1, the halogen atom is a chlorine atom.

The —NR$_2$ radical in formula I is an amido grouping bound covalently to the metal atom. Amine compounds which are bound datively to the central metal atom only by way of the free electron pair are not considered as amido groupings in the sense of this invention.

The metallocenamide chlorides of the invention can contain, as metallocene ligands L, all π systems known for this purpose, or suitable linked or unlinked π systems. Suitable systems are known to those versed in the art. Cyclopentadienyl (Cp), indenyl (Ind) and fluorenyl (Flu) radicals, maybe substituted, can be cited as preferred examples of such systems. There can be two individual ligands present, which are the same or different, or a ligand that is linked bivalently to M and contains two π systems, or a metallocene ligand that has one π system and is linked with M via another radical. For the invention, therefore, L$_2$ does not necessarily mean that 2 separate ligands have to be present, but much rather the possibility of 2 valences of M being occupied by a bivalent ligand L. Bivalent ligands of this kind can, for example, contain two identical or different π systems, for example, possibly substituted Cp, Ind or Flu, which are interbridged and each of which is bound to the metal atom. However, it is also possible for just one π ligand system to be present, to which, in turn, the radical R* is bound. The radical R* forms the second bond with the metal atom. The radical R* can have all the meanings described later for the metallocenamide halides of the invention. Suitable metallocene ligands are known to those versed in the art, and can be taken, for example, from the literature sources EP 0 495 099 and PCT/WO90/07526. Within the framework of this invention, especially preferred ligands are, for example, the dimethylsilyl (tetramethylcyclopentadienyl)tert.-butylamido grouping and the (CH$_3$)$_2$Si(Ind)$_2$ grouping, or groupings which are substituted otherwise at the π ligand.

For this invention, it is to advantage to use aluminum alkyls or boron co-catalysts, in particular methylaluminoxan MAO, together with the metallocenamide halide of formula I in the catalyst system of the invention.

In principle, the compounds of formula 1 can also be present in the catalyst system of the invention as mixtures, or as mixtures with other metallocenes, half-sandwich compounds or traditional Ziegler-Natta catalysts. As cocatalyst, furthermore, any compound is suitable which can convert the metallocenamide halide of formula 1 into a cation and stabilize it.

The catalyst systems of the invention are distinguished by being extremely active; markedly less co-catalyst is required, especially when MAO is used, than for catalysts and catalyst systems known hitherto, in particular the metallocene dichlorides or diamides.

Also subject matter of this invention are metallocenamide halides of formula I,

in which
 L is a metallocene ligand,
 Hal is a halogen from the group comprising F, Cl, Br and I,
 M is a metal from group III, IV or V of the periodic table or from the lanthanide series, and
 R stands for identical or different, straight-chain or branched, saturated or unsaturated hydrocarbon radicals with up to 8 carbon atoms, where the amido group $NR_2$ can also form a heterocycle with up to 8 carbon atoms, maybe incorporating further heteroatoms.

The $—NR_2$ radical is an amido grouping bound covalently to the metal atom. Amine compounds which are bound datively to the central metal atom only by way of the free electron pair are not considered as amido groupings in the sense of this invention.

The metallocenamide halides of the invention can be used to particular advantage as components in catalyst systems according to the invention. In this invention, the two substituents L attached to the metal can together also represent a bivalent, bridged ligand.

A bivalent, bridged ligand of this kind can be bound to the metal by way of two π ligand systems, for example; ie, it can contain, for example, two cyclopentadienyl or indenyl units, maybe. in substituted form, which are interconnected and each of which is bound to the metal atom. Alternatively, there may be just one π ligand system present, to which, in turn, a radical R* is bound, which forms the second bond with the metal atom. The radical R* can form a bridge of arbitrary make-up to the metal; once again, it is preferable within the framework of the invention if R* is a hydrocarbon chain with up to 5, or better, up to 3 atoms in the chain; the chain may, in addition, be substituted and may contain heteroatoms.

It is especially preferable if the radical R* is bound via an amido group to the metal. In another especially preferred embodiment, R* contains a silyl group, and in particular a dimethylsilyl group.

For the metallocenamide halides of the invention and the metallocene ligands L, just as for the catalyst system of the invention containing these compounds, use can be made, in principle, of all already known metallocene ligands or metallocene ligands which were found later to be suitable. For this invention, however, it is especially preferable if both metallocene ligands are present in the form of a bridged, bivalent ligand. Bridged ligand systems of this kind, too, are described in the already-mentioned literature sources.

In the case of two unbridged π systems being bound to the metal atom, it is beneficial if these ligands are substituted asymmetrically with alkyl or maybe alkyl-substituted aryl groups. Special preference is given here to substituted Cp, in particular n-butyl-Cp or Cp substituted in the 1,2- or 1,3 positions with butyl and methyl, Indenyl radicals are preferably substituted with an aromatic radical, which, in turn, can itself carry one or more alkyl groups.

Within the framework of this invention it is preferable if the metallocenamide halide contains titanium, zirconium or hafnium as metal. The preferred halogen for this invention is chlorine, although bromine compounds are also well suited.

The metallocenamide halides of the invention, with the formula 1, can be synthesized by reacting the dihalides with a molar equivalent of alkali amide (eg, lithium amide):

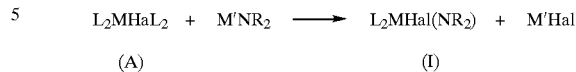

This step can be conducted with good yields, but the metallocene dihalides needed as starting compounds are, for their part, often obtainable in yields of only 15 to 20%.

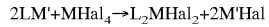

Besides these low yields, the synthesis of metallocene dihalides is associated with a number of other unpleasant production stages and disadvantages. For example, the reaction often has to be conducted at a very low temperature, which is a technical disadvantage. Another problem is purification, because the major portion of waste product (M'Hal) is formed along with the product itself during the last stage of the synthesis. This means that the actual purification, ie, the separation of rac and meso forms, can only ensue after the product has been extracted from the waste.

According to prior art, the dichloro compound A can also be obtained from the diamino compound B, eg, by reacting B with halogenosilane:

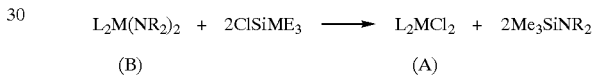

However, the disadvantage here is that B, insofar as it is not better to prepare it from A, can indeed only be obtained from ligands L and a homoleptic transition metal amide, with amine being split off, if the ligands are only hindered sterically to a small extent (Jordan, U.S. Pat. No. 5,597,935).

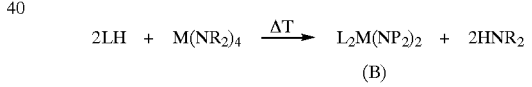

A further object of this invention was thus to provide an easy and productive method of synthesizing, among other compounds, metallocenamide halogens of formula 1.

This object is established according to the invention by a method of preparing compounds with the general formula (II)

in which
 L is a metallocene ligand,
 Hal is a halogen atom from the group comprising F, Cl, Br and I,
 M is a metal from one of the groups III, IV or V of the periodic table or from the lanthanide series, and
 R stands for identical or different, straight-chain or branched, saturated or unsaturated hydrocarbon radicals with up to 8 carbon atoms, where the amido group $NR_2$ can be a heterocycle with up to 8 carbon atoms, maybe incorporating further heteroatoms, and, when x=1, y is 1, 2 or 3 and z is 3, and when x=2, y is 1 or 2 and z is 2, by reacting a metallocene ligand LH with a compound of formula (III)

in which M and R have the meanings given above and w is a whole number from 1 to 3.

Surprisingly, it was found within the framework of this invention that mixed (heteroleptic) metal amide halides (III) can be reacted with ligands LH directly to mixed metallocenamide halides of formula 1 or also to metallocene dihalides A. Amazingly, the amine which is released does not result in a halogen-amide exchange at the metallocene center.

In the method of the invention, L, M and Hal have the meanings already given above for compounds of formula 1.

Depending on the composition of the transition metal starting compound of formula III, it is possible according to the invention to determine the end products right at the start of the synthesis. One embodiment of the invention thus provides for the following reaction to take place:

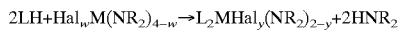

where w and y are both 1 or both 2.

(2 LH can, in this case, also mean HL-LH, in which case a compound is obtained with a divalent, bridged ligand).

One has the choice of producing the conventional metallocene dichlorides where y=2, or the novel metallocenamide chlorides of the invention, where y=1. In any case, no salt burden is formed as by-product during the last and decisive step of the synthesis, and no tedious product extraction is required. The rac-meso separation can be carried out immediately. An additional disadvantage of the traditional synthesis, namely the low-temperature reaction conditions, is also avoided. Instead, the synthesis is conducted at an elevated temperature (>100° C., preferably about 160–170° C.), which is technically easier to realize.

An important advantage of the synthetic path according to the invention is that there are no limitations in respect of the organic radical attached to the metallocene ligand. All hitherto known linked π systems (Cp (which may be substituted); Ind and Flu systems (which may be substituted)) can be incorporated into the future catalyst by means of this reaction. Of particular importance, however, is the fact that there are no problems with substituents in the 2-position on the indent backbone.

And precisely these substituents are of particular importance, because the corresponding catalysts are among the most sought-after of their kind. This is because the polymers synthesized with these catalysts are distinguished by having high molecular weights.

The synthesis of the invention is not limited to two unbridged ligands or one divalent, bridged ligand, but can be considered quite generally for the introduction of organic ligands with weakly acidic protons into transition metal complexes.

This makes it possible also to prepare metal complexes with only one π ligand (eg, Cp*MHal$_3$), which are likewise used in the field of polymerization.

To this end, a starting compound with the composition monoamidohalogenometal-substance can be reacted with the ligand in question.

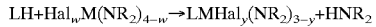

where w=y=1, 2 or 3.

The reaction conditions and the advantages are the same as those already described for the method of the invention.

In preferred embodiments of the invention, the cyclopentadienyl-, indenyl- or fluorenyl compounds, which may be substituted, are used in the synthesis as metallocene ligands. As already explained, these ligands can be used as two individual ligands which are identical or different, or, equally well, as bridged ligands, or as a single ligand which saturates two valences of the metal atom by way of an additional radical R* or a heteroatom. It is of advantage to use titanium, zirconium or hafnium as metal.

In an especially preferred embodiment of the invention, a new metallocenamide halide as provided for by the invention, in particular a metallocenamide chloride, is synthesized according to the method of the invention.

Additional subject matter of the invention is the use of the metallocenamide halides of the invention, with the formula 1, to generate an active catalyst system for (co)polymerization reactions. It is especially beneficial to use aluminum alkyls or boron co-catalysts, preferably methylaluminoxan (MAO), together with the metallocenamide halide.

The following examples serve to explain the invention in more detail:

EXAMPLE 1

Preparation of dichloro[dimethylsilyl(tetramethylcyclopentadienyl)tert-butylmido] titanium (IV)

In an inert-gas atmosphere, 283 mg (1.368 mmol) dichloro-bis(dimethylamido)titanium (IV) are weighed out and dissolved in 15 ml mesitylene. To this solution, 344 mg (1368 mmol) (tetramethylcyclopentadienyldimethylsilyl)tert-butylamine are added at room temperature. The solution is then refluxed for 1 ¼ hours (165° C.). The solvent is distilled off under reduced pressure, and the residue extracted with hexane. The product can be isolated in crystalline form by means of subsequent crystallization.

Characterization:

$^1$H-NMR (400 MHz, CDCl$_3$, 25° C.): δ[ppm]=0.69 ((CH$_3$)$_2$Si, 6H), 1.42 (tertbutyl, 9H), 2.12 (CH$_3$, 6H), 2.22 (CH$_3$, 6H).

$^{13}$C-NMR (100 MHz, CDCl$_3$, 25° C.): δ[ppm]=5.5, 13.1, 17.3, 32.6, 62.3, 126.9, 138.1, 140.9.

EXAMPLE 2

Preparation of (chloro)(dimethylamido)[dimethylsilyl(tetramethylcyclopentadienyl)tert-butylamido]titanium(IV)

In an inert-gas atmosphere, 190 mg (0.516 mmol) dichloro[dimethylsilyl(tetramethylcyclopentadienyl)tert-butylamido]titanium and 26 mg (0.510 mmol) lithium dimethylamide are weighed out and dissolved in 20 ml hexane at room temperature. The reaction mixture is stirred for 30 min at room temperature and refluxed for 1.5 hours. After the solution has been filtered, the solvent is partially distilled off under reduced pressure and crystallized at −30° C. The product is obtained as a red crystalline solid.

Characterization:

$^1$H NMR (400 MHz, CDCl$_3$, 25° C.): δ[ppm]=0.50 ((CH$_3$)$_2$Si, 3H), 0.56 ((CH$_3$)$_2$Si, 3H), 1.39 (tertbutyl, 9H), 1.63 (CH$_3$, 3H), 1.94 (CH$_3$, 3H), 2.12 (CH$_3$, 6H), 2.80 (N(CH$_3$)$_2$, 6H).

EXAMPLE 3

Preparation of chloro-bis(dimethylamido)[dimethylsilyl(tetramethylcyclopentadienyl)tert-butylamin]titanium(IV)

In an inert-gas atmosphere, 408 mg (1.893 mmol) chloro tris(dimethylamido)titanium(IV) are weighed out and dissolved in 20 ml mesitylene. To this solution, 476 mg (1.893 mmol) (tetramethylcyclopentadienyldimethylsilyl)tertbutylamine are added. The solution was then refluxed for 1 ¼ hours (111° C.). The solution is freed of the solid fraction by means of filtration, and the solvent distilled off under reduced pressure. The resulting product is almost pure.

Characterization:

$^1$H-NMR (400 MHz, CDCl$_3$, 25° C.): δ[ppm]=0.09 ((CH$_3$)$_2$Si, 6H), 1.08 (tertbutyl, 9H), 1.83 (CH$_3$, 6H), 2.00 (CH$_3$, 6H), 3.03 (N(CH$_3$)$_2$, 12H).

EXAMPLE 4

Preparation of trichloro (pentamethylcyclopentadienyl)titanium(IV)

In an inert-gas atmosphere, 210 mg (1.059 mmol) trichlorodimethylamidotitanium(IV) are weighed out and dissolved in 15 ml mesitylene. This solution is cooled to −50° C., and 145 mg (1.059 mmol) pentamethylcyclopentadiene are injected into it. The solution is then refluxed for 1 ½ hours (165° C.). After the solvent has been removed by distillation under reduced pressure, the residue is extracted with hexane. After subsequent removal of the extraction solvent, the product can be isolated.

Characterization:

$^1$H-NMR (400 MHz, CDCl$_3$, 25° C.): δ[ppm]=1.89 (C$_5$(CH$_3$)$_5$).

$^{13}$C-NMR (100 MHz, CDCl$_3$, 25° C.): δ[ppm]=14.0 (C$_5$(CH$_3$)$_5$), 137.27 (C$_5$(CH$_3$)$_5$).

EXAMPLE 5

Preparation of rac-chloro[η$^5$:η$^5$-bis(1-indenyl)dimethylsilyl](dimethylamido)-zirconium In an inert-gas atmosphere, ZrCl[N(CH$_3$)$_2$]$_3$ (184 mg, 0.711 mmol) and (CH$_3$)$_2$Si(IndH)$_2$ (205 mg, 0.711 mmol) are dissolved in 20 ml mesitylene at room temperature. This solution is then heated in an oil bath to the boiling point of the solvent, and refluxed for 2.5 hours. The oil-bath heating is switched off, and the mesitylene removed from this hot solution by means of distillation under a reduced pressure of 8·10$^{-4}$ Pa. The temperature of the oil bath decreases as the solvent is removed, and can be raised again by means of a hot-water bath. The residue is extracted with 30 ml toluene, and concentrated to its turbidity point at room temperature. The solution is now cooled slowly to −30° C., and rac-(CH$_3$)$_2$Si(Ind)$_2$ZrCl[N(CH$_3$)$_2$] is isolated as a red crystalline solid.

Characterization:

$^1$H-NMR (400 MHz, C$_6$D$_6$, 25° C.): δ[ppm]=0.82, 0.94 ((CH$_3$)$_2$Si, 6H), 2.51 (N(CH$_3$)$_2$, 6H), 6.04–7.68 (12H).

$^{13}$C-NMR (100 MHz, C$_6$D$_6$, 25° C.): δ[ppm]=−2.30, −1.15 ((CH$_3$)$_2$Si), 48.21 (N(CH$_3$)$_2$), 111–135 (aromat. C)).

EXAMPLE 6

Preparation of rac-chloro[η$^5$:η$^5$-bis(1-indenyl)dimethylsilyl](dimethylamido)-hafnium In an inert-gas atmosphere, HfCl[N(CH$_3$)$_2$]$_3$ (312 mg, 0.901 mmol) and (CH3)$_2$Si(IndH)$_2$ (260 mg, 0.901 mmol) are dissolved in 25 ml mesitylene at room temperature. This solution is heated in an oil bath to the boiling point of the solvent, and refluxed for 2.5 hours. The oil-bath heating is switched off and the mesitylene removed from this hot solution by distillation under reduced pressure of 8·10$^{-4}$ Pa. The temperature of the oil bath decreases as the solvent is removed, and can be raised again by means of a hot-water bath. The residue is extracted with toluene and recrystallized several times until the product can be isolated as a red crystalline solid.

Characterization:

$^1$H-NMR (400 MHz, C$_6$D$_6$, 25° C.): δ[ppm]=0.69, 0.73 ((CH$_3$)$_2$Si, 6H), 2.52 (N(CH$_3$)$_2$, 6H), 5.89–7.54 (12H).

$^{13}$C-NMR (100 MHz, C$_6$D$_6$, 25° C.): δ[ppm]=−2.29, −1.12 ((CH$_3$)$_2$Si), 47.82 (N(CH$_3$)$_2$), 110–135 (aromat. C)).

EXAMPLE 7

Preparation of rac-chloro[η$^5$:η$^5$-bis(2-methylinden-1-yl)dimethylsilyl](dimethyl-amido)zirconium In an inert-gas atmosphere, ZrCl[N(CH$_3$)$_2$]$_3$ (425 mg, 1.642 mmol) and (CH$_3$)$_2$Si(2-Me-IndH)$_2$ (520 mg, 1.642 mmol) are dissolved in 20 ml mesitylene at room temperature. This solution is heated in an oil bath to the boiling point of the solvent, and refluxed for 3 hours. The oil-bath heating is switched off and the mesitylene removed from this hot solution by distillation under a reduced pressure of 8·10$^{-4}$ Pa. The temperature of the oil bath decreases as the solvent is removed, and can be raised again by means of a hot-water bath. The residue is extracted with toluene and recrystallized several times until the product can be isolated as a red crystalline solid.

Characterization:

$^1$NMR (400 MHz, C$_6$D$_6$, 25° C.: δ[ppm]=0.80, 0.88 ((CH$_3$)$_2$Si, 6H), 2.25, 2.27 ((CH$_3$)Ind, 6H), 2.60 (N(CH$_3$)$_2$, 6H), 6.50–7.71 (12H).

$^{13}$C-NMR (100 MHz, C$_6$D$_6$, 25° C.): δ[ppm]=2.10, 2.44 ((CH$_3$)$_2$Si), 17.38, 18.16 ((CH$_3$)Ind) 49.40 (N(CH$_3$)$_2$), 115–135 (aromat. C)).

EXAMPLE 8

Preparation of rac-bromo[η$^5$:η$^5$-bis(1-indenyl)dimethylsilyl](dimethylamido)-zirconium In an inert-gas atmosphere, 198 mg (0.653 mmol) ZrBr[NMe$_2$]$_3$ and 188 mg (0.652 mmol) Me$_2$Si(IndH)$_2$ are dissolved in 10 ml toluene, after which the solvent is distilled off again. The solid remaining behind is heated to 110° C., which causes it to fuse. After 30 minutes, the melt is heated to room temperature. The red substance is taken up in 5 ml toluene, and separated from the insoluble solids fraction by means of filtration. After repeated recrystallization from toluene and hexane at −30° C., the desired complex can be isolated.

$^1$H-NMR (400 MHz, C$_6$D$_6$, 25° C.): [ppm]δ=0.58 (s, 3H, Si(CH$_3$)$_2$), 0.72 (s, 3H, Si(CH$_3$)$_2$), 2.46 (s, 6H, N(CH$_3$)$_2$), 5.91 (d, 1H, $^3$J (H,H)=3.08 Hz, 5-ring), 5.98 (d, 1H, $^3$J(H,H)=3.28 Hz, 5-ring), 6.59 (dd, 1H, $^3$J(H,H)=7.44 Hz, $^3$J(H,H)=7.69 Hz, 6-ring), 6.73 (d, 1H, $^3$J(H,H)=3.24 Hz, 5-ring), 6.85 ("dd", 1H, $^3$J(H,H)=7.53 Hz, $^3$J(H,H)=7.60 Hz, 6-ring), 6.93 ("dd", 1H, $^3$J(H,H)=7.53 Hz, 6-ring), 6.96 ("dd", 1H, $^3$J(H,H)=8.80 Hz, 6-ring), 7.04 ("dd", 1H, $^3$J(H,H)=7.75 Hz, $^3$J(H,H)=7.90 Hz, 6-ring), 7.18 ("t", 1H, $^3$J(H,H)=9.02 Hz, 6-ring), 7.32 (dd, 1H, $^3$J(H,H)=9.07 Hz, $^3$J(H,H)=8.65 Hz, 6-ring), 7.44 (dd, 1H, $^3$J(H,H)=7.06 Hz, $^3$J(H,H)=8.43 Hz, 6-ring), 7.49 (d, 1H, $^3$J(H,H)=8.58 Hz, 6-ring).

EXAMPLE 9

Preparation of rac-[η$^5$:η$^5$-bis(1-indenyl)-dimethylsilyl](iodo)(dimethylamido)-zirconium In an inert-gas atmosphere, 347 mg (0.990 mmol) ZrI[NMe$_2$]$_3$ and 286 mg (0.990 mmol) Me$_2$Si(IndH)$_2$ are dissolved in 10 ml toluene, after which the solvent is distilled off again. The solid remaining behind is heated to 110° C., which causes it to fuse. The melt is kept for 30 minutes under reduced pressure. After 30 minutes, it is heated to room temperature. The red substance is taken up in 5 ml toluene, and separated from the insoluble solids fraction by means of filtration. After repeated recrystallization from toluene and hexane at −30° C., the desired complex can be isolated.

$^1$H-NMR (400 MHz, $C_6D_6$, 25° C.): [ppm]δ=0.53 (s, 3H, Si(C$\underline{H}_3$)$_2$), 0.70 (s, 3H, Si(C$\underline{H}_3$)$_2$), 2.42 (s, 6H, N(C$\underline{H}_3$)$_2$), 5.83 (d, 1H, $^3$J(H,H)=3.02 Hz, 5-ring), 6.00 (d, 1H, $^3$J(H,H)=3.27 Hz, 5-ring), 6.57 (dd, 1H, $^3$J(H,H)=7.34 Hz, $^3$J(H,H)=7.60 Hz, 6-ring), 6.65 (d, 1H, $^3$J(H,H)=3.09 Hz, 5-ring), 6.86 (m, 2H, 6-ring), 7.16 (m, 1H, 6-ring), 7.26 (d, 1H, $^3$J(H,H)=9.12 Hz, 6 ring), 7.28 (d, 1H, $^3$J(H,H)=8.55 Hz, 6-ring), 7.49 (m, 3H, 6-ring).

EXAMPLE 10

Preparation of rac-chloro[η$^5$:η$^5$-2,2-bis(1-indenyl)propandiyl](dimethylamido)-zirconium In an inert-gas atmosphere, 174 mg (0.672 mmol) ZrCl [N(CH$_3$)$_2$]$_3$ and 183 mg (0.672 mmol) 2,2-bis(indenyl)propane are weighed out and dissolved in 10 ml mesitylene. The reaction solution is refluxed for 2 hours at 165° C., during which time the color turns dark red. The solvent is distilled off under reduced pressure, and replaced by toluene. Following a filtration step, the reaction mixture is concentrated and cooled to −30° C. to induce crystallization. The product can be isolated as a red crystalline solid.

$^1$H-NMR (400 MHz, d$^8$-thf, 25° C.): [ppm]δ=2.22 (s, 3H, C8C$\underline{H}_3$)$_2$), 2.39 (s, 3H, C(C$\underline{H}_3$)$_2$), 2.44 (s, 6H, N(C$\underline{H}_3$)$_2$), 6.14 (d, 1H, $^3$J(H,H)=3.51 Hz, 5-ring), 6.54 (d, 1H, $^3$J(H,H)=3.51 Hz, 5-ring), 6.59 ("d", 2H, $^3$J(H,H)=3.51 Hz, 5-ring), 6.75 (dd, 1H, $^3$J(H,H)=6.52 Hz, 6-ring), 6.87 (m, 1H, 6-ring), 7.01 (m, 2H, 6-ring), 7.30 (d, 1H, $^3$J(H,H)=8.64 Hz, 6-ring), 7.52 (d, 1H, $^3$J(H,H)=8.53 Hz, 6-ring), 8.04 (d, 1H, $^3$J(H, H)=8.53 Hz, 6-ring).

EXAMPLE 11

Preparation of rac-chloro[η$^5$:η$^5$-bis(2-methyl-4,5-benzinden-1-yl)dimethylsilyl](diemethylamido) zirconium In an inert-gas atmosphere, 230 mg (0.888 mmol) ZrCl [N(CH$_3$)$_2$]$_3$ and 370 mg (0.888 mmol) bis(2-methyl-4,5-benzindenyl)dimethylsilane are weighed out and dissolved in 10 ml mesitylene. The reaction solution is refluxed for 2 hours at 165° C., during which time the color turns dark red. The solvent is distilled off under reduced pressure, and replaced by toluene. Following a filtration step, the reaction mixture is concentrated and cooled to −30° C. to induce crystallization. The product can be isolated as a red crystalline solid.

$^1$H-NMR (400 MHz, $C_6D_6$, 25° C.): [ppm]δ=0.86 (s, 3H, Si(C$\underline{H}_3$)$_2$), 0.91 (s, 3H, Si(C$\underline{H}_3$)$_2$), 2.03 (s, 6H, N(C$\underline{H}_3$)$_2$), 2.37 (s, 3H, 2-$\underline{Me}$Ind), 2.39 (s, 3H, 2-$\underline{Me}$Ind), 7.00–7.88 (m, 14H, Benz-Indenyl).

EXAMPLE 12

Preparation of rac-dichloro[η$^5$:η$^5$-bis(1-indenyl)dimethylsilyl]zirconium

In an inert-gas atmosphere, 220 mg (0.763 mmol) bis(indenyl)dimethylsilane and 301 mg (0.763 mmol) di(chloro)bis(dimethylamido)bis(tetrahydrofurano)zirconium are weighed out and suspended in 20 ml mesitylene. After two hours of refluxing at 165° C., the reaction solution is cooled to room temperature and the solvent distilled off under reduced pressure. The residue is taken up in toluene and freed of the insoluble fraction by means of filtration. The volume of solvent is reduced, and the solution recrystallized at −30° C.

$^1$H-NMR (400 MHz, CDCl$_3$, 25° C.): [ppm]δ=1.12 (s, 6H, Si(C$\underline{H}_3$)$_2$), 6.08 (d, 2H, 5-ring), 6.90 (d, 2H, 5-ring), 7.04–7.60 (m, 8H, aromat.)

EXAMPLE 13

Preparation of rac-dichloro[η$^5$:η$^5$-bis(2-methyl-4,5-benzinden-1-yl)dimethylsilyl]zirconium In an inert-gas atmosphere, 322 mg (0.773 mmol) bis(2-methyl-4,5-benzindenyl)dimethylsilane and 305 mg (0.773 mmol) di(chloro)bis(dimethyamido)bis(tetrahydrofurano)zirconium are weighed out and dissolved in 20 ml mesitylene and 5 ml THF. The reaction solution is refluxed for 2 hours at 165° C., and then cooled slowly to room temperature. The solvent is removed and the residue taken up in toluene. Following filtration, the solvent is concentrated and the product recrystallized at −30° C.

$^1$H-NMR (400 MHz, CDCl$_3$, 25° C.): [ppm]δ=1.37 (s, 6H, Si(C$\underline{H}_3$)$_2$), 2.38 (s, 6H, 2-$\underline{Me}$Ind), 7.20–7.98 (m, 14H, aromat.)

EXAMPLE 14

Preparation of rac-chloro[η$^5$:η$^5$-bis-1,2-(1-indenyl)ethandiyl](dimethylamido) zirconium In an inert-gas atmosphere, 1.214 g (2.9 mmol) rac (CH$_2$Ind)$_2$ZrCl$_2$ and 0.170 g (3.3 mmol) LiNMe$_2$ are dissolved/suspended in 30 ml toluene. The reaction mixture is then refluxed for 3 hours. After cooling, it is filtered, and the solvent removed from the filtrate by means of distillation. After drying, the complex can be isolated as a red powder.

$^1$H-NMR (200 MHz, $C_6D_6$, 25° C.) [ppm]δ=2.52 (s, 6H, N(C$\underline{H}_3$)$_2$), 2.83–3.45 (m, 4H, (C$\underline{H}_2$)$_2$), 5,59 (d, 1H, 5-ring), 5.97 (d, 1H, 5-ring), 6.31 (dd, 1H, 5-ring), 6.44 (dd, 1H, 5-ring), 6.58–7.49 (m, 8H, 6-ring).

EXAMPLE 15

Chloro[η$^5$:η$^5$-bis(n-butylcyclopentadienyl)](dimethylamido)hafnium

In an inert-gas atmosphere, 10 g (20.33 mmol) (nBuCp)$_2$HfCl$_2$ and 1.04 g (20.33 mmol) LiNMe$_2$ are dissolved/suspended in 100 ml toluene. The reaction mixture is refluxed for 3 hours, and then filtered at room temperature. Following removal of the solvent by distillation, and high-vacuum drying, the complex can be isolated as a brown oil.

$^1$H-NMR (200 MHz, $C_6D_6$, 25° C.) [ppm]δ=0.86 (t, 6H, CH$_2$-C$\underline{H}_3$), 1.17–1.53 (m, 8H, C$\underline{H}_2$), 2.36–2.71 (m, 4H C$\underline{H}_2$), 2.92 (s, 6H, N(C$\underline{H}_3$)$_2$), 5.46–5.50 (m, 2H, 5-ring), 5.53–5.57 (m, 2H, 5-ring), 5.83–5.88 (m, 2H, 5-ring), 5.91–5.94 (m, 2H, 5-ring)

EXAMPLE 16

Chloro[η$^5$:η$^5$-bis(n-butylcyclopentadienyl)](dimethylamido)zirconium

In an inert-gas atmosphere, 14.834 g (36.67 mmol) (nBuCP)$_2$ZrCl$_2$ and 1.871 g (36.67 mmol) LiNMe$_2$ are dissolved/suspended in 100 ml toluene. The reaction mixture is refluxed for 3 hours, and then filtered at room temperature. Following removal of the solvent by distillation, and high-vacuum drying, the complex can be isolated as a brown oil.

$^1$H-NMR (200 MHz, $C_6D_6$, 25° C.): [ppm]δ=0.86 (t, 6H, $CH_2$—$C\underline{H}_3$), 1.18–1.55 (m, 8H, $C\underline{H}_2$), 2.39–2.69 (m, 4H, $C\underline{H}_2$), 2.86 (s, 6H, $N(CH_3)_2$), 5.49–5.52 (m, 2H, 5-ring), 5.57–5.62 (m, 2H, 5-ring), 5.85–5.90 (m, 2H, 5-ring), 5.99–6.02 (m, 2H, 5-ring)

$^{13}$C-NMR (50 MHz, $C_6D_6$, 25° C.) [ppm]δ=14.12 ($CH_2$—$\underline{C}H_3$), 22.80/30.12/33.53 (—$\underline{C}H_2$—), 50.45 (N($\underline{C}H_3)_2$), 107.66/110.04/111.74/114.54/131.79 (5-ring)

EXAMPLE 17

After being rendered inert, a 0.5-liter stirred reactor is filled at room temperature with 0.24 l toluene and 5 ml 10% MAO, and the mixture heated to a polymerization temperature of 40° C. The solution is then saturated under a pressure of 2 bar with gaseous propane.

5 mg bis(indenyl)dimethylsilylenzirconium(dimethyl) amide chloride are dissolved in 50 ml toluene, and 3.1 ml 10% MAO are added. 6 ml of this stock solution are transferred to the stirred reactor at the start of polymerization. After an hour, the reaction mixture is quenched with HCl-containing ethanol. One obtains 19.8 g isotactic polypropylene with a melting point of 144° C. and an isotacticity of 94%.

EXAMPLE 18

After being rendered inert, a 0.5-liter stirred reactor is filled at room temperature with 0.24 l toluene and 3 ml 25 wt % tri-isobutylaluminum, and the mixture heated to a polymerization temperature of 40° C. The solution is then saturated under a pressure of 2 bar with gaseous propene.

5 mg bis(indenyl)dimethylsilylenezirconium(dimethyl) amide chloride are dissolved in 50 ml toluene, and 3.1 ml 10% MAO are added. 4 ml of this stock solution are transferred to the stirred reactor at the start of polymerization. After an hour, the reaction mixture is quenched with HCl-containing ethanol. One obtains 22.3 g isotactic polypropylene with a melting point of 144.7° C. and an isotacticity of 93.5%.

EXAMPLE 19

After being rendered inert, a 0.5-filter stirred reactor is filled at room temperature with 0.24 1 toluene and 3 ml 25 wt % tri-isobutylaluminum, and the mixture heated to a polymerization temperature of 60° C. The solution is then saturated under a pressure of 2 bar with gaseous propene.

5 mg bis(indenyl)dimethylsilylenezirconium(dimethyl) amide chloride are dissed in 50 ml toluene, and 3.1 ml 10% MAO are added. 2.5 ml of this stock solution are transferred to the stirred reactor at the start of polymerization. After an hour, the reaction mixture is quenched with HCl-containing ethanol. One obtains 9.3 g isotactic polypropylene with a melting point of 133° C. and an isotacticity of 90.5%.

What is claimed is:

1. A catalyst system for (co)polymerization reactions, containing a metallocenamide halide of formula (I)

in which

L is a metallocene ligand,

Hal is a halogen from the group comprising F, Cl, Br and I,

M is a metal from group III, IV or V of the periodic table or from the lanthanide series, and R stands for identical or different, straight-chain or branched, saturated or unsaturated hydrocarbon radicals with up to 8 carbon atoms, where the amido group $NR_2$ can also form a heterocycle with up to 8 carbon atoms, maybe incorporating further heteroatoms, and a co-catalyst.

2. The catalyst system of claim 1, wherein
the metal is titanium, zirconium or hafnium.

3. The catalyst system of claim 1, wherein
Hal stands for chlorine.

4. The catalyst system of claim 1, wherein
the metallocene ligand is selected from cyclopentadienyl-, indenyl- or fluorenyl-groupings, each of which may be substituted.

5. A catalyst system according to one of the preceding claims, wherein
the system contains alkylaluminumoxan or a boron co-catalyst as co-catalyst.

6. The catalyst system of claim 5, wherein
the system contains MAO.

7. A metallocenamide halide of the formula $$Hal\text{-}L_2M\text{-}NR_2 \tag{I}$$

wherein
L is a metallocene ligand, with the exception of unsubstituted or doubly alkyl-substituted, non-bridged cyclopentadienyl;

Hal is a halogen selected from the group consisting of F, Cl, Br and I;

M is a metal from group III, IV or V of the periodic table or from the lanthanide series; and R stands for identical or different, straight-chain or branched, saturated or unsaturated hydrocarbon radicals with up to 8 carbon atoms; wherein the arnido group $NR_2$ can also form a heterocycle with up to 8 carbon atoms, optionally incorporates further heteroatoms.

8. The metallocenamide halide of claim 7, wherein both substituents L attached to the metal together represent a bivalent, bridged ligand.

9. The metallocenamide halide of claim 8, wherein the bivalent, bridged ligand is bound to the metal by way of two π ligands.

10. The metallocenamide halide of claim 8, wherein the divalent, bridged ligand is bound to the metal by way of a π ligand and a radical R* attached thereto, the radical R* being a hydrocarbon chain of up to 5 atoms' length, which optionally contains heteroatoms.

11. The metallocenamide halide of claim 10, wherein the radical R* contains an amido group via which it is bound to the metal.

12. The metallocenamide halide of claim 10, wherein R* contains a silyl group.

13. The metallocenamide halide of claim 12, wherein said silyl group is dimethylsilyl.

14. A metallocenamide halide according to claim 7, wherein the metal is selected from the group consisting of titanium, zirconium and hafnium.

15. A metallocenamide halide according to claim 7, wherein Hal is chlorine.

16. A metallocenamide halide according to claim 7, wherein the metallocene ligand or the a ligand is a ligand selected from the group consisting of cyclopentadienyl, indenyl and fluorenyl compounds, each of which may be substituted.

17. A method of generating an active catalyst system for copolymerization reacting comprising combining metallocenamide halides of formula $Hal-L_2M-NR_2$ with a suitable co-catalyst and the desired monomer; wherein L is a metallocene ligand;

Hal is a halogen from the group comprising F, Cl, Br and I;

M is a metal from group III, IV or V of the periodic table or from the lanthanide series, and R stands for identical or different, straight-chain or branched, saturated or unsaturated hydrocarbon radicals with up to 8 carbon atoms, where the amido group $NR_2$ can also form a heterocycle with up to 8 carbon atoms, maybe incorporating further heteroatoms, with a suitable combination with a co-catalyst with the desired monomer.

18. The method of claim 17, wherein the metallocene ligands used are selected from the group comprising cyclopentadienyl, indenyl and fluorenyl compounds, each of which may be substituted.

19. The method of claim 17, wherein compounds of formula (II) are isolated, in which x=2.

20. The method of claim 19, wherein a divalent, bridged ligand is used as ligand LH.

21. The method of claim 17, wherein the divalent, bridged ligand is bound to the metal by way of 2 π ligands.

22. The method of claim 21, wherein the divalent, bridged ligand is bound to the metal by way of a π ligand and a radical R* attached thereto, the radical R* being a hydrocarbon chain with a chain length of up to 5 atoms and which may be substituted and may contain heteroatoms.

23. The method of claim 22, wherein the radical R* contains an amido group, via which it is bound to the metal.

24. The method of claim 22, wherein R* contains a silyl group.

25. The method of claim 17, wherein titanium, zirconium or hafnium is used as metal M.

26. A method according to claim 18, wherein Hal in at least one of formulas II and III is chlorine.

27. A method according to claim 17, wherein a metallocenamide chloride is synthesized.

28. The method of claim 24, wherein R* is dimethylsilyl.

* * * * *